US009779376B2

(12) United States Patent
Dubbels et al.

(10) Patent No.: US 9,779,376 B2
(45) Date of Patent: Oct. 3, 2017

(54) DYNAMICALLY ALLOCATING BUSINESS WORKFLOWS

(75) Inventors: Joel C. Dubbels, Eyota, MN (US); Richard J. Stevens, Rochester, MN (US)

(73) Assignee: International Business Machines Corporation, Armonk, NY (US)

( * ) Notice: Subject to any disclaimer, the term of this patent is extended or adjusted under 35 U.S.C. 154(b) by 1235 days.

(21) Appl. No.: 13/181,561

(22) Filed: Jul. 13, 2011

(65) Prior Publication Data

US 2013/0018693 A1 Jan. 17, 2013

(51) Int. Cl.
*G06Q 10/00* (2012.01)
*G06Q 10/06* (2012.01)
*G06Q 50/22* (2012.01)

(52) U.S. Cl.
CPC ......... *G06Q 10/0633* (2013.01); *G06Q 50/22* (2013.01)

(58) Field of Classification Search
CPC ............................ G06Q 10/0633; G06Q 50/22
USPC ........................................................ 705/7.27
See application file for complete search history.

(56) References Cited

U.S. PATENT DOCUMENTS

| | | | |
|---|---|---|---|
| 5,600,554 A | 2/1997 | Williams | |
| 6,226,745 B1 | 5/2001 | Wiederhold | |
| 6,256,613 B1 | 7/2001 | Falchuk et al. | |
| 6,260,021 B1 | 7/2001 | Wong et al. | |
| 6,401,138 B1 | 6/2002 | Judge et al. | |
| 6,574,629 B1 | 6/2003 | Cooke et al. | |
| 6,763,344 B1 | 7/2004 | Osentoski et al. | |
| 6,842,736 B1 | 1/2005 | Brzozowski | |
| 6,941,131 B2 | 9/2005 | Roderique | |
| 6,941,313 B2 | 9/2005 | Seliger et al. | |
| 7,043,714 B2 | 5/2006 | Lin et al. | |
| 7,127,448 B1 | 10/2006 | Wong | |
| 7,133,833 B1 | 11/2006 | Chone et al. | |
| 7,302,609 B2 | 11/2007 | Matena et al. | |
| 7,395,436 B1 | 7/2008 | Nemovicher | |
| 7,406,691 B2 | 7/2008 | Fellenstein et al. | |
| 7,522,175 B2 | 4/2009 | Morita et al. | |
| 7,742,933 B1 | 6/2010 | Royds | |
| 7,864,995 B2 * | 1/2011 | Fidrich et al. | 382/128 |

(Continued)

OTHER PUBLICATIONS

"Accelerating medical research using the swift workflow system", SP Tiberiu, B Clifford, I Foster . . .—Studies in health . . . , 2007—ncbi.nlm.nih.gov.*

(Continued)

*Primary Examiner* — Alan S Miller
*Assistant Examiner* — Folashade Anderson
(74) *Attorney, Agent, or Firm* — Brandon C. Kennedy; Grant A. Johnson; Kennedy Lenart Spraggins LLP

(57) ABSTRACT

Dynamically allocating business workflows, each workflow comprising a reusable component of a business transaction, including: receiving, by a workflow orchestrator, a request for a business transaction; determining, by the workflow orchestrator, a desired result for the business transaction in dependence upon the request; selecting, by the workflow orchestrator, one or more workflows from a set of available workflows in dependence upon the request and the desired result; determining an execution order for the one or more workflows; and executing, by the workflow orchestrator, the one or more selected workflows in the execution order.

6 Claims, 10 Drawing Sheets

(56) References Cited

U.S. PATENT DOCUMENTS

| | | | |
|---|---|---|---|
| 7,930,193 B2 | 4/2011 | Marx | |
| 8,041,749 B2 | 10/2011 | Beck | |
| 8,108,878 B1* | 1/2012 | Pulsipher | 718/106 |
| 8,145,503 B2 | 3/2012 | Backhaus et al. | |
| 8,195,481 B2 | 6/2012 | Backhaus | |
| 8,380,809 B2 | 2/2013 | Becker et al. | |
| 8,712,120 B1 | 4/2014 | Reicher et al. | |
| 8,949,427 B2 | 2/2015 | Dubbels et al. | |
| 9,042,617 B1 | 5/2015 | Reicher et al. | |
| 2002/0035638 A1 | 3/2002 | Gendron et al. | |
| 2003/0013951 A1 | 1/2003 | Stefanescu et al. | |
| 2004/0252348 A1 | 12/2004 | Desai | |
| 2005/0028079 A1 | 2/2005 | Dinh et al. | |
| 2005/0192979 A1* | 9/2005 | Keller et al. | 707/100 |
| 2006/0230072 A1 | 10/2006 | Partovi et al. | |
| 2007/0055977 A1 | 3/2007 | Becker et al. | |
| 2007/0136814 A1 | 6/2007 | Lee et al. | |
| 2007/0186106 A1 | 8/2007 | Ting et al. | |
| 2007/0192408 A1 | 8/2007 | Konig | |
| 2007/0203748 A1 | 8/2007 | Rothpearl et al. | |
| 2007/0292012 A1 | 12/2007 | Brandon et al. | |
| 2008/0016111 A1 | 1/2008 | Keen | |
| 2008/0046328 A1 | 2/2008 | Paron et al. | |
| 2008/0086526 A1 | 4/2008 | Jianzhong et al. | |
| 2008/0126121 A1 | 5/2008 | Kirohey et al. | |
| 2008/0140454 A1 | 6/2008 | Hernandez et al. | |
| 2008/0163070 A1 | 7/2008 | Mahesh et al. | |
| 2008/0168567 A1 | 7/2008 | Hahn et al. | |
| 2008/0219557 A1* | 9/2008 | Dawson et al. | 382/187 |
| 2008/0312963 A1 | 12/2008 | Reiner | |
| 2009/0025063 A1 | 1/2009 | Thomas | |
| 2009/0147988 A1 | 6/2009 | Jones et al. | |
| 2009/0150184 A1 | 6/2009 | Spahn | |
| 2009/0217340 A1 | 8/2009 | Sitomer et al. | |
| 2009/0228299 A1 | 9/2009 | Kangarloo et al. | |
| 2010/0172567 A1 | 7/2010 | Prokoski | |
| 2010/0205485 A1 | 8/2010 | Tashiro et al. | |
| 2010/0256994 A1 | 10/2010 | Eisenberger et al. | |
| 2011/0110568 A1 | 5/2011 | Vesper et al. | |
| 2011/0191781 A1 | 8/2011 | Karanam et al. | |
| 2011/0288877 A1 | 11/2011 | Ofek et al. | |
| 2012/0221346 A1* | 8/2012 | Acker et al. | 705/2 |
| 2012/0221354 A1 | 8/2012 | Wall | |
| 2012/0221535 A1 | 8/2012 | Dubbels et al. | |
| 2012/0221728 A1 | 8/2012 | Dubbels et al. | |
| 2013/0018662 A1 | 1/2013 | Dubbels et al. | |
| 2013/0018693 A1 | 1/2013 | Dubbels et al. | |
| 2013/0018694 A1* | 1/2013 | Dubbels et al. | 705/7.27 |
| 2013/0046537 A1* | 2/2013 | Weeks et al. | 704/235 |
| 2013/0046547 A1 | 2/2013 | Drucker et al. | |
| 2013/0185092 A1 | 7/2013 | Dubbels et al. | |
| 2013/0208955 A1* | 8/2013 | Zhao | G06F 19/321 382/128 |
| 2013/0218620 A1 | 8/2013 | Liu et al. | |
| 2016/0246788 A1* | 8/2016 | Thangaraj | G06F 3/04842 |

OTHER PUBLICATIONS

Globus MEDICUS—federation of DICOM medical imaging devices into healthcare Grids. SG Erberich, JC Silverstein, A Chervenak . . .—Studies in health . . . , 2007 —ncbi.nlm.nih.gov.*
A medical image archive solution in the cloud CC Teng, J Mitchell, C Walker, A Swan . . .-. . . ICSESS), 2010 IEEE . . . , 2010—ieeexplore.ieee.org.*
Mobile healthcare information management utilizing Cloud Computing and Android OS C Doukas, T Pliakas . . .—Conf Proc IEEE Eng Med . . . , 2010—urania.cs.ntou.edu.tw.*
High-performance cloud computing: A view of scientific applications C Vecchiola, S Pandey, R Buyya—. . . Systems, Algorithms, and . . . , 2009—ieeexplore.ieee.org.*
"Gridifying a Diffusion Tensor Imaging Analysis Pipeline" MWA Caan, FM Vos, AHC van Kampen . . .-. . . and Grid Computing . . . , Univ of Amsterdam Medical Conference, May 17-20, 2010—ieeexplore.ieee.org.*
A knowledge-based imaging informatics approach to managing patients treated with proton beam therapy B Liu, HK Huang, M Law, A Le . . .-. . . Medical Imaging, 2007—spiedigitallibrary.org.*
Mage-assisted knowledge discovery and decision support in radiation therapy planning BJ Liu, MYY Law, J Documet, A Gertych— Computerized Medical Imaging . . . , 2007—Elsevier.*
"Accelerating medical research using the swift workflow system", SP Tiberiu, B Clifford, I Foster . . .—Studies in Health . . . 2007—ncbi.nlm.nih.gov.
Globus MEDICUS—federation of DICOM medical imaging devices into healthcare Grids. SG, JC Silverstein A. Chervenak . . ._Studies in health . . . ,2007—ncbi.nlm.nih.gov.
A medical image archive solution in the cloud CC Teng, J Mitchell, C Walker, A Swan . . .-. . . ICESS), 2010 IEEE . . . ,2010— ieeexplore.ieee.org.
Mobile healthcare information management utilizing Cloud Computing and Android OS C Doukas, T Pilakas . . .—Conf Proc IEEE Eng Med . . . ,2010-arania.cs.ntou.edu.tw.
High-Performance cloud computing: A view of scientific applications C Vecchiola, S. Pandey, R Buyya—. . . Systems, Algorithm, and . . . ,2009—ieeexplore.ieee.org.
Gridifying a Diffusion Tensor Imaging Analysis Pipeline MWA Caan, FM Vos, AHS can Kampen . . .-. . . and Grid Computing . . . , Univ of Amsterdam Medical Conference, May 17-20, 2010—ieeexplore.ieee.org.
Image-assisted knowledge discovery and decision support in radiation therapy planning BJ Liu, MYY Law, Ja Documet, A Gertych-Computerized Medical Imaging . . . ,2007—Elsevier.
Workflow management for paramedical emergency operations within a mobile-static distributed environment A Riposan, VV Patriciu—Proceeding of the 4th Workshop on Workflows . . . , 2009—DL.acm.org.
Cloud computing: A new business paradigm for biomedical information sharing A Rosenthal, P Mork, MH Li . . ._Journal of . . . 2010—cloud.pubs.dbs.uni-leipzig.de.
Office Action, U.S. Appl. No. 13/035,196, Dec. 20, 2012.
Office Action, U.S. Appl. No. 13/035,229, Mar. 14, 2013.
Office Action, U.S. Appl. No. 13/035,030, Jan. 22, 2013.
Office Action, U.S. Appl. No. 13/181,561, Mar. 29, 2013.
Office Action, U.S. Appl. No. 13/211,656, Apr. 11, 2013.
Office Action, U.S. Appl. No. 13/181,127, Jan. 28, 2013.
Stef-Praun, T., et al., "Accelerating Medical Research using the Swift Workflow System" NIH Public Access Author Manuscript, Available in PMC May 2, 2009, pp. 207-216, Published in final edited form as: Studies in Health Technology and Informatics, vol. 126, 2007, NIH, Bethesda, MD, USA. PMCID: PMC2676238, URL: http://www.ncbi.nlm.nih.gov/pmc/articles/PMC2676238/.
Final Office Action, U.S. Appl. No. 13/035,196, Oct. 9, 2013, pp. 1-20.
Office Action, U.S. Appl. No. 13/035,196, Jun. 26, 2013, pp. 1-20.
Final Office Action, U.S. Appl. No. 13/035,000, Aug. 27, 2013, pp. 1-17.
Office Action, U.S. Appl. No. 13/035,000, May 17, 2013, pp. 1-19.
Office Action, U.S. Appl. No. 13/035,229, Sep. 6, 2013, pp. 1-28.
Final Office Action, U.S. Appl. No. 13/035,030, May 30, 2013, pp. 1-21.
Office Action, U.S. Appl. No. 13/181,245, Aug. 28, 2013, pp. 1-19.
Final Office Action, U.S. Appl. No. 13/211,656, Aug. 13, 2013, pp. 1-10.
Final Office Action, U.S. Appl. No. 13/181,127, Jul. 15, 2013, pp. 1-19.
Final Office Action, U.S. Appl. No. 13/688,914, Oct. 9, 2013, pp. 1-15.
Office Action, U.S. Appl. No. 13/688,914, Jun. 27, 2013, pp. 1-17.
Office Action, U.S. Appl. No. 13/690,741, Aug. 29, 2013, pp. 1-20.
DICOM Standards Committee, "Digital Imaging and Communications in Medicine (DICOM)—*Supplements 135: SR Diagnostic Imaging Report Transformation Guide*", Aug. 24, 2010, 79 pages, DICOM Standards Committee, Rosslyn, Virginia.

(56) References Cited

OTHER PUBLICATIONS

Teng, "Managing DICOM Image Metadata with Desktop Operating Systems Native User Interface", Apr. 7, 2009, 5 pages, Brigham Young University, Provo, Utah.
UltraRad, "Automated DICOM Pre-fetch for Legacy Applications using UltraPREFETCH" Oct. 20, 2008, 5 pages, UltraRad Corporation, West Berlin, New Jersey.
Hermen et al., "Managing and Viewing DICOM Images with ImageJ", Oct. 2008, 6 pages, Luxembourg Institute of Science and Technology (LIST), Luxembourg.
Zhao et al., "Realizing Fast, Scalable and Reliable Scientific Computations in Grid Environments", in Grid Computing Research Progress, Chapter 1, pp. 1-40, Oct. 2008, Nova Science Publishers, Inc., Commack New York.

\* cited by examiner

Medical Image Business Object 118

Request ID 302
Request Type 304
Action ID 306
Provider ID 308
Patient ID 310
Physician ID 312
Technician ID 314
Scanner ID 316
Scanner Type 318
Image ID 320
Image Type 322
Patient Location 324
Destination Location 326
Receiving Gateway ID 328
Destination Gateway ID 330

Original Image Pointer 332
Interim Image Pointer 334
Resultant Image Pointer 336

Image Provider Protocol 338

FIG. 3

DYNAMICALLY ALLOCATING BUSINESS WORKFLOWS

BACKGROUND OF THE INVENTION

Field of the Invention

The field of the invention is data processing, or, more specifically, methods, apparatus, and products for administering medical digital images in a distributed medical digital image computing environment.

Description of Related Art

Current medical image management systems are inflexible and do not support a model of accessing any and all medical images produced across a multi-facility enterprise. This causes the data from analyzing these images to be difficult to share and difficult to produce.

SUMMARY OF THE INVENTION

Methods, systems, and computer program products are provided for dynamically allocating business workflows, including: receiving, by a workflow orchestrator, a request for a business transaction; determining, by the workflow orchestrator, a desired result for the business transaction in dependence upon the request; selecting, by the workflow orchestrator, one or more workflows from a set of available workflows in dependence upon the request and the desired result; determining an execution order for the one or more workflows; and executing, by the workflow orchestrator, the one or more selected workflows in the execution order. The foregoing and other objects, features and advantages of the invention will be apparent from the following more particular descriptions of exemplary embodiments of the invention as illustrated in the accompanying drawings wherein like reference numbers generally represent like parts of exemplary embodiments of the invention.

BRIEF DESCRIPTION OF THE DRAWINGS

FIG. 3 sets forth a block diagram of an example medical image business object according to embodiments of the present invention.

DETAILED DESCRIPTION OF EXEMPLARY EMBODIMENTS

Figure 1:
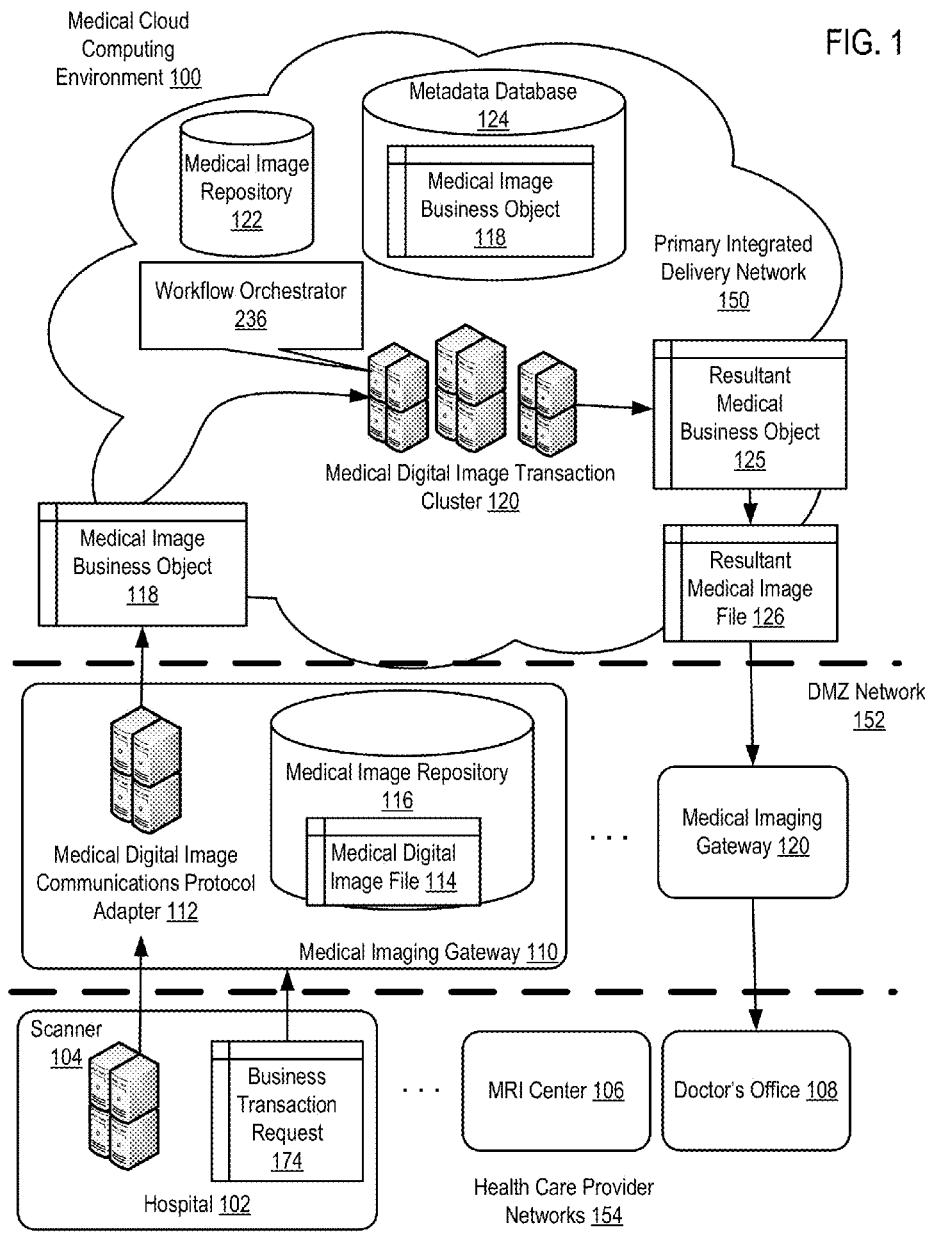
FIG. 1 sets forth a network diagram of a system for administering a medical digital images in a distributed medical digital image computing environment and dynamically allocating business workflows according to embodiments of the present invention.

Exemplary methods, systems, and products for administering medical digital images in a distributed medical digital image computing environment and dynamically allocating business workflows in accordance with the present invention are described with reference to the accompanying drawings, beginning with FIG. 1. FIG. 1 sets forth a network diagram of a system for administering a medical digital images in a distributed medical digital image computing environment and dynamically allocating business workflows according to embodiments of the present invention. The system of FIG. 1 includes a distributed processing system implemented as a medical cloud computing environment (100). Cloud computing is a model of service delivery for enabling convenient, often on-demand network access to a shared pool of configurable computing resources such as networks, network bandwidth, servers, processing, memory, storage, applications, virtual machines, and services that can be rapidly provisioned and released with reduced management effort or interaction with the provider of the service. This cloud model often includes five characteristics, three service models, or four deployment models.

Characteristics of the cloud model often include on-demand self-service, broad network access, resource pooling, rapid elasticity, and measured service. On-demand self-service is a characteristic in which a cloud consumer can often unilaterally provision computing capabilities, such as server time and network storage, as needed automatically without requiring human interaction with the cloud service provider.

Broad network access is a characteristic describing capabilities that are available over a network and accessed through standard mechanisms that promote use by heterogeneous thin or thick client platforms such as mobile phones, laptops, desktop computers, PDAs, and so on as will occur to those of skill in the art.

Resource pooling is a characteristic in which the cloud service provider's computing resources are pooled to serve multiple consumers using a multi-tenant model, with different physical and virtual resources dynamically assigned and reassigned according to demand. There is often a sense of location independence in that the consumer generally has no control or knowledge over the exact location of the provided resources but may be able to specify a location at a higher level of abstraction such as the country, state, datacenter and so on.

Rapid elasticity is a characteristic in which the capabilities of the cloud computing environment can be rapidly and elastically provisioned, in some cases automatically, to quickly scale out and rapidly released to quickly scale in. To the consumer of the cloud computing environment, the capabilities available for provisioning often appear to be unlimited and appear to be able to be purchased in any quantity at any time.

Measured service is a characteristic in which cloud systems automatically control and optimize resource use by leveraging a metering capability at some level of abstraction appropriate to the type of service such as storage, processing, bandwidth, active user accounts, and so on. Resource usage often can be monitored, controlled, and reported providing transparency for both the provider and consumer of the utilized service. Examples of service models often implement in the cloud computing environment include software as a service ('SaaS'), platform as a service ('PaaS') and infrastructure as a service ('IaaS'). SaaS typically provides the capability to the consumer to use the provider's applications running on a cloud infrastructure. The applications often are accessible from various client devices through a thin client interface such as a web browser, web-based e-mail client, and so on. The consumer often does not manage or control the underlying cloud infrastructure including network, servers, operating systems, storage, or even individual application capabilities, with the common possible exception of limited user-specific application configuration settings.

PaaS typically includes the capability provided to the consumer to deploy onto the cloud infrastructure consumer-created or acquired applications created using programming languages and tools supported by the cloud service provider. The consumer often does not manage or control the underlying cloud infrastructure including networks, servers, operating systems, or storage, but has control over the deployed applications and possibly application hosting environment configurations.

IaaS typically includes the capability provided to consumers to provision processing, storage, networks, and other fundamental computing resources where the consumers are able to deploy and run arbitrary software, which can include operating systems and applications. The consumers often do not manage or control the underlying cloud infrastructure but have control over operating systems, storage, deployed applications, and possibly limited control of select networking components such as, for example, host firewalls.

Example deployment models often used in cloud computing environments include private clouds, community clouds, public clouds, and hybrid clouds. In a private cloud deployment model, the cloud infrastructure often is operated solely for an organization. It may be managed by the organization or a third party and may exist on-premises or off-premises. In the community cloud deployment model, the cloud infrastructure is shared by several organizations and supports a specific community that has shared concerns such as, for example, mission, security requirements, policy, compliance considerations, and so on. It may be managed by the organizations or a third party and may exist on-premises or off-premises. In the public cloud deployment model, the cloud infrastructure is made available to the general public or a large industry group and is owned by an organization selling cloud services. In the hybrid cloud deployment model, the cloud infrastructure is a composition of two or more clouds, such as private, community, public, that remain unique entities but are bound together by standardized or proprietary technology that enables data and application portability such as, for example, cloud bursting for load-balancing between clouds.

A cloud computing environment is generally considered service oriented with a focus on statelessness, low coupling, modularity, and semantic interoperability. At the heart of cloud computing is an infrastructure comprising a network of interconnected nodes. The distributed processing computing environment of FIG. 1 includes a medical imaging cloud computing environment (100). The medical imaging cloud computing environment (100) of FIG. 1 is capable of administering medical digital images according to embodiments of the present invention. In the example of FIG. 1 the medical imaging cloud computing environment (100) includes two networks: a primary integrated delivery network (150) and a DMZ network (152). The primary integrated delivery network (150) of FIG. 1 is a highly secure network for administering image processing transactions upon medical images according to aspects of embodiments of the present invention. The DMZ network (152), or demilitarized zone, of FIG. 1 is a physical or logical sub-network that contains and exposes the medical imaging cloud computing environment's external services to the larger untrusted network, such as the Internet, through which the health care provider networks (154) may access the services of the medical imaging cloud computing environment. The DMZ network (152) of FIG. 1 adds an additional layer of security to the medical imaging cloud because an external attacker only has access to equipment in the DMZ, rather than any other part of the medical imaging cloud.

The medical cloud computing environment (100) of FIG. 1 includes medical imaging cloud gateway (110) in the DMZ network (152). The medical imaging cloud gateway (110) in the DMZ network (152) includes a medical digital image communications protocol adapter (112), a module of automated computing machinery that is capable of receiving a medical digital image from a provider of medical images such as a hospital (102), MRI center (106), doctor's office, and so on as will occur to those of skill in the art. The medical digital image communications protocol adapter (112) is capable of receiving the medical image according to any number of protocols supported by the providers of the medical images such as Digital Imaging and Communications in Medicine ('DICOM'), Health Level Seven ('HL7'), and others as will occur to those of skill in the art.

DICOM is a standard for handling, storing, printing, and transmitting information in medical imaging. DICOM includes a file format definition and a network communications protocol. The communication protocol is an application protocol that uses TCP/IP to communicate between systems. DICOM files can be exchanged between two entities that are capable of receiving image and patient data in DICOM format. DICOM enables the integration of scanners, X-ray machines, cameras, ultrasound machines and so on, an servers, workstations, printers, and network hardware from multiple manufacturers into a picture archiving and communication system (PACS).

HL7 is an all-volunteer, non-profit organization involved in development of international healthcare standards. HL7 is also used to refer to some of the specific standards created by the organization. HL7 and its members provide a framework and related standards for the exchange, integration, sharing, and retrieval of electronic health information.

In the example of FIG. 1 a medical image is created by scanner (104) in a hospital (102) and sent to the medical imaging cloud gateway (110) according to a protocol supported by the hospital (102). Often such medical images range in size from 50 to 500 kilobytes, but they can be both bigger and smaller. Each image is often called a slice and often many slices together make a series of images that are processed together for medical treatment. A series may contain a single image or thousands of images. Examples of scanners useful in producing medical images according to embodiments of the present invention include magnetic resonance scanners, computed tomography scanners, digital radiography scanners and many others as will occur to those of skill in the art. Many manufacturers produce such scanners such as General Electric, Siemens, and others.

The example of a scanner (104) in a hospital (102) is for explanation and not for limitation. In fact, medical images that may be administered according to embodiments of the present invention may be created in any health care setting such as clinics, MRI centers (106), doctor's offices (108) and many others as will occur to those of skill in the art.

The medical digital image communications protocol adapter (112) of FIG. 1 receives a request for an image processing transaction to process the medical digital image. The request is transmitted according to one of a plurality of a medical image communications protocol supported by medical digital image communications protocol adapter and used by a producer of the medical images. The request may be received according to any number of protocols supported by the provider of the digital image such as DICOM, HL7, and others as will occur to those of skill in the art. The request received in the medical digital image protocol adapter (112) contains a medical image to be processed, metadata describing the medical image, and an identification of the processing to be performed on the image.

An image processing transaction is request to perform one or more image processing workflows on one or more medical images in the medical imaging cloud computing environment. A workflow is typically implemented as one or more services, reusable components of data processing. The services of the workflow are bound together and executed to carry out the workflow. Such workflows often include analytics for tumor detection, tumor growth, aneurysm detection, vessel separation in a patients head, and many other medical conditions, workflows for image compression, image resolution, distribution of images, and many other workflows for medical image processing that will occur to those of skill in the art.

The medical digital image communications protocol adapter (112) of FIG. 1 parses the request according to the contents of the request and the structure of the request defined by the protocol and standard in which the request was created and extracts one or more the medical images associated with the request and metadata describing the request and the medical images. The medical digital image communications protocol adapter (112) of FIG. 1 creates, in dependence upon classification rules and the contents of the request, a medical image business object representing the business transaction. A medical image business object is a data structure that represents the requested business transaction, includes metadata describing the request and the medical images processed in the requested transaction. The medical image business object has predefined structure. In some embodiments the medical image business object may be implemented as an XML file or other structured documents.

Classification rules are rules that are tailored to parsing the request according to the protocol and standard in which in which the request was created to extract medical images and metadata. The classification rules are also tailored to develop the medical image business object by including the extracted images and metadata in a predefined structure in the medical image business object. Classification rules allow for disparate metadata, arriving in disparate protocols and standards to be read, understood classified and organized according to a defined structure for the medical image business object.

In the example of FIG. 1, the medical image communications protocol adapter (112) sends the medical image business object to a medical digital image transaction cluster (120) that stores the medical image business object in the medical image metadata database.

In the example of FIG. 1, the medical image communications protocol adapter (112) may store the medical images (114) locally in a medical image repository on the medical imaging gateway or the medical image communications protocol adapter (112) may send the medical images (114) to the medical digital image transaction cluster (120) which may store the images in a medical image repository (122) in the primary integrated delivery network (150).

The medical digital image transaction cluster (120) of FIG. 1 selects, in dependence upon workflow selection rules and the attributes of the medical image business object, one or more medical analytic workflows to process the medical image. Workflow selection rules are rules that are tailored to carrying out the image processing transaction on the medical images and the medical image business object according to the request received by the health care provider. Such workflow selection rules identify the necessary requirements of the transaction and select workflows having services that carry out those requirements as well as select workflows that are tailored for the attributes of those images such as the slice size, number of slices, type of scanner used to create the images, standards used for the images and many others as will occur to those of skill in the art. Workflows may include analytics for tumor detection, tumor growth, aneurysm detection, vessel separation in a patients head, and many other medical conditions, workflows for image compression, image resolution, distribution of images, and many other workflows for medical image processing that will occur to those of skill in the art.

The medical digital image transaction cluster (120) of FIG. 1 process the medical image of the request with the medical analytic workflows, thereby creating a resultant business object (125) and resultant medical image (126). Processing the medical image is typically carried out by executing the selected medical analytic workflows and creating results for transmission to the health care provider.

The medical digital image transaction cluster (120) of FIG. 1 routes, in dependence upon content routing rules and the attributes of the resultant business object, the resultant medical image to a destination. Examples of destinations in FIG. 1 include the hospital (102), MRI center (106), and a doctor's office (108) each in one or more networks for health care providers (154). The example destinations of FIG. 1 are for explanation and not for limitation. In fact, embodiments of the present invention may route the resultant medical image to many different destinations such as other hospitals, clinics, houses of doctors, patients, technicians, workstations, PDAs and many others as will occur to those of skill in the art.

Content routing rules are rules dictating the manner in which resultant medical images are routed to the destination. Such rules are often based on the content of the resultant medical image such that the image is routed to an appropriate health care provider in a manner that conforms to both security and privacy. Often the destination of the image is a different location, logical or physical, from the provider of the original medical image prior to its being processed by the medical digital image transaction cluster. Content routing rules may also dictate the manner in which the health care provider may access the resultant medical images and who may access such images.

Routing the resultant medical image to a destination according to the example of FIG. 1 includes extracting metadata from the resultant business object, creating a response to the request the response conforming to a particular digital image communications protocol used for the destination, and transmitting the response according to the particular digital image communications protocol supported by the destination such as, for example, DICOM, HL7, and others as will occur to those of skill in the art.

Routing the resultant medical image to a destination according to the example of FIG. 1 may include storing the resultant medical image on a gateway within the medical digital image computing environment assigned to a destination of the medical image and transmitting the response according to the particular digital image communications protocol further comprises transmitting in the response data access information to access the resultant medical image on the gateway.

Routing the resultant medical image to a destination also often includes sending a notification describing the resultant medical image to the destination. Examples of such a notification may be an email message or a text message to a health care provider notifying the health care provider that the response to the request is ready for viewing or that the workflows processing the medical images identified aspects of the images that are consistent with a medical condition such as tumor, aneurism, vessel separation, and so on as will occur to those of skill in the art. In the example of FIG. 1, the original business objects and original medical images may be stored such that at a later time the new medical image business objects may be created in dependence upon the classification rules and attributes of the selected business object. In such embodiments one or more medical analytic workflows to process the medical image may be selected and used to process the medical images differently.

Medical cloud computing environment (100) of FIG. 1 is not limited to administering medical images. The medical cloud computing environment (100) is also useful in dynamically allocating business workflows according to embodiments of the present invention.

In the example of FIG. 1, the medical imaging gateway (110) receives from a user a request (174) for execution of a business transaction within the medical cloud computing environment (100). For example, the medical imaging gateway (110) may receive from a user a request (174) to transmit medical imaging data over the medical cloud computing environment (100). The medical imaging gateway (100) is capable of receiving the request (174) for execution of a business transaction according to a number of protocols. In the example of FIG. 1, the medical imaging gateway (110) sends the request (174) for execution of a business transaction to the medical digital image transaction cluster (120) of the primary integrated delivery network (150).

The example of FIG. 1 includes a workflow orchestrator (236) in the medical digital image transaction cluster (120). In the example of FIG. 1, the workflow orchestrator (236) is a module of automated computing machinery for identifying workflows that are used to carry out a business transaction, organizing the workflows to carrying out a business transaction, and executing a business transaction by utilizing the workflows. The workflow orchestrator (236) may include special purpose computer program instructions for identifying workflows that are used to carry out a business transaction, organizing the workflows to carrying out a business transaction, and executing a business transaction by utilizing the workflows, and so on.

In the example of FIG. 1, the workflow orchestrator (236) determines a desired result for the business transaction in dependence upon the request (174). In the example of FIG. 1, each type of request (174) for execution of a business transaction may be associated with a particular output type such that the desired result for the business transaction may correlate to the output type of the request (174) for execution of a business transaction. For example, if the request (174) for execution of a business transaction is a request to transfer a medical image, the desired result for the business transaction may include transferring a medical image.

In the example of FIG. 1, the workflow orchestrator (236) also dynamically selects workflows from a set of available workflows in dependence upon the request (174) and the desired result. In the example of FIG. 1, the workflow orchestrator (236) may also dynamically select workflows from a set of available workflows in dependence upon the metadata associated with the request (174). In the example of FIG. 1, the request (174) for execution of a business transaction may include input parameters of a particular type. Because the desired result has been determined, the workflow orchestrator (236) must therefore select an available workflow that not only takes input parameters of the particular type that are included in the request (174) for execution of a business transaction, but also is capable of generating the desired result alone or in combination with other workflows. Consider, for example, the following table identifying the set of all available workflows:

TABLE 1

Set of Available Workflows

| Workflow ID | Input Parameter Type | Output Parameter Type |
| --- | --- | --- |
| 1 | A | B |
| 2 | B | C |
| 3 | A | C |
| 4 | B | A |
| 5 | A | A |
| 6 | C | B |

In the example of Table 1, six workflows are identified with workflow IDs of 1, 2, 3, 4, 5, and 6. Consider an example in which a request (174) for execution of a business transaction is received that include input parameters of type 'A' and a desired result of type 'C.' In such an example, the workflow identified by a workflow ID of '3' may be selected. Alternatively, a combination of workflows may be selected such that the workflows identified by workflow IDs of '1' and '2' may be used to carry out the requested business transaction if the request (174) for execution of a business transaction is first executed by the workflow identified by a workflow ID of '1,' which subsequently passes its results to the workflow identified by a workflow ID of '1.' Alternative combinations of workflows are also available.

In the example of FIG. 1, the workflow orchestrator (236) also executes the selected workflows. In the example of FIG. 1, executing the selected workflows may be carried out, for example, by the workflow orchestrator (236) calling a particular workflow and passing information included in the request (174) for execution of a business transaction to the workflow as an input parameter. Alternatively, executing the selected workflows may be carried out by the workflow orchestrator (236) calling a particular workflow and passing information that was returned as output from another workflow to the particular workflow as an input parameter.

The arrangement of servers and other devices making up the exemplary system illustrated in FIG. 1 are for explanation, not for limitation. Data processing systems useful according to various embodiments of the present invention may include additional servers, routers, other devices, peer-to-peer architectures, databases containing other information, not shown in FIG. 1, as will occur to those of skill in the art. Networks in such data processing systems may support many data communications protocols, including for example Transmission Control Protocol ('TCP'), Internet Protocol ('IP'), HyperText Transfer Protocol ('HTTP'), Wireless Access Protocol ('WAP'), Handheld Device Transport Protocol ('HDTP'), and others as will occur to those of skill in the art. Various embodiments of the present invention may be implemented on a variety of hardware platforms in addition to those illustrated in FIG. 1.

Figure 2:
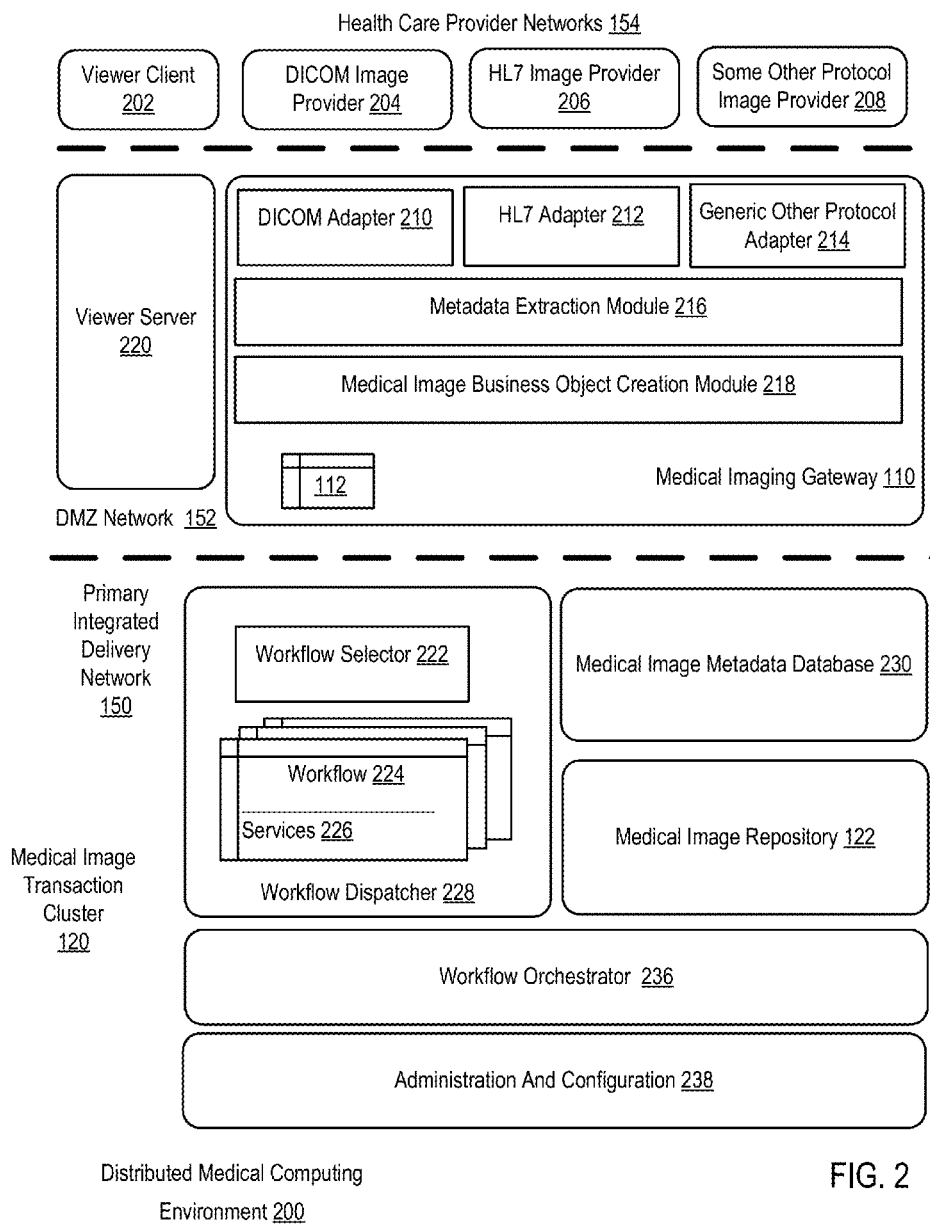
FIG. 2 sets forth an example system for administering medical digital images and dynamically allocating business workflows in a distributed medical computing environment.

For further explanation, FIG. 2 sets forth an example system for administering medical digital images and dynamically allocating business workflows in a distributed medical computing environment (200). The medical computing environment of FIG. 2 includes two networks, a DMZ network (152) and a primary integrated delivery network (150). The distributed medical computing environment (200) administers medical digital images for a number of health care providers who provide medical images and receives the results of imaging transactions processed on those medical images, and also dynamically allocates business workflows, according to embodiments of the present invention. The distributed medical computing environment may be implemented as a cloud computing environment that is accessible to the health care providers through the health care provider networks (154).

The example distributed medical image computing environment (200) of FIG. 2 includes a medical imaging gateway (110), a module of automated computing machinery that includes a DICOM adapter (210), an HL7 adapter (212), generic other protocol adapter (214), a metadata extraction module (216) and a medical image business object creation module (218). The medical imaging gateway (110) of FIG. 2 receives, in one of the medical digital image communications protocol adapter (210, 212, 214), a request for an image processing transaction to process the medical digital image. The request contains a medical image to be processed, metadata describing the medical image, and an identification of the processing to be performed on the image.

The request is transmitted according to one of a plurality of a medical image communications protocol supported by medical digital image communications protocol adapter and used by a producer of the medical images. In the example of medical imaging gateway (110) is capable of receiving a request for an image processing transaction from a health care provider (204) according to the DICOM standard, a health care provider (206) that produces medical images according to the HL7 standard, or some other health care providers (208) using other protocols and standards for creating and transmitted medical digital images.

The DICOM adapter (210) is capable of receiving and parsing the request according to the DICOM standard, the HL7 Adapter (212) is capable of receiving and parsing a request according the HL7 standard, and the generic other protocol adapter (214) is capable of receiving an parsing the request according to some other protocol that will occur to those of skill in the art.

The metadata extraction module (216) of FIG. 1 extracts the metadata from the parsed request according to the standards and protocol used to create and transmit the request and provides the extracted metadata to the medical image business object creation module that creates, in dependence upon classification rules and the contents of the request, a medical image business object (112) representing the business transaction. The medical image business object includes a predefined structure and may be implemented as a structured document such as an XML document.

The medical imaging gateway (110) of FIG. 2 sends the medical image business object (112) to a medical image transaction cluster (120) in the primary integrated delivery network. The medical image transaction cluster (120) includes a workflow dispatcher (228), a medical image metadata database (230), a medical image repository (122), a security module (232), and a medical imaging cloud computing administration and configuration module (238). The workflow dispatcher (228) receives the medical image business object and stores the medical image business object (112) in the medical image metadata database (230) and stores the medical image in the medical image repository (122). The workflow dispatcher (228) of FIG. 2 includes a workflow selector (222) that select, in dependence upon workflow selection rules and the attributes of the medical image business object, one or more medical analytic workflows to process the medical image.

The workflow dispatcher (228) processes the medical image of the request with the medical analytic workflows, thereby creating a resultant business object and resultant medical image. The workflow dispatcher (228) routes, in dependence upon content routing rules and the attributes of the resultant business object, the resultant medical image to a destination.

The workflow dispatcher (228) of FIG. 2 routes the resultant medical image to a destination by extracting metadata from the resultant business object, creating a response to the request the response conforming to a particular digital image communications protocol used for the destination, and transmitting the response according to the particular digital image communications protocol.

The workflow dispatcher (228) of FIG. 2 may route the resultant medical image to a destination by storing the resultant medical image on the medical imaging gateway (110) assigned to the destination of the medical image. The workflow dispatcher may then transmit in the response data access information to access the resultant medical image on the gateway. Alternatively, it is also possible to send the resultant image(s) to a destination using capabilities inherent in protocols such as DICOM. A health care provider may then view the resultant medical images using the viewer server (220) in the DMZ network (152) through the use of a viewer client (202) at the health care provider's location.

The distributed medical computing environment (200) is also capable of dynamically allocating business workflows according to embodiments of the present invention. In the example of FIG. 2, the workflow orchestrator (236) is a module of automated computing machinery for identifying workflows that are used to carry out a business transaction, organizing the workflows to carrying out a business transaction, and executing a business transaction by utilizing the workflows. The workflow orchestrator (236) may include special purpose computer program instructions for identifying workflows that are used to carry out a business transaction, organizing the workflows to carrying out a business transaction, and executing a business transaction by utilizing the workflows, and so on.

In the example of FIG. 2, the workflow orchestrator (236) receives a request for a business transaction and determines a desired result for the business transaction in dependence upon the request. Each request for execution of a business transaction in FIG. 2 may be associated with a particular output type such that the desired result for the business transaction may correlate to the output type of the request for execution of a business transaction. For example, if the request for execution of a business transaction is a request to transfer a medical image, the desired result for the business transaction may include transferring a medical image.

In the example of FIG. 2, the workflow orchestrator (236) also dynamically selects workflows from a set of available workflows in dependence upon the request and the desired result. In the example of FIG. 2, the request for execution of a business transaction may include input parameters of a particular type. Because the desired result has been determined, the workflow orchestrator (236) must therefore select an available workflow that not only takes input parameters of the particular type that are included in the request for execution of a business transaction, but also is capable of generating the desired result alone or in combination with other workflows.

In the example of FIG. 2, the workflow orchestrator (236) also executes the selected workflows. Executing the selected workflows may be carried out, for example, by the workflow orchestrator (236) calling a particular workflow and passing information included in the request for execution of a business transaction to the workflow as an input parameter. Alternatively, executing the selected workflows may be carried out by the workflow orchestrator (236) calling a particular workflow and passing information that was returned as output from another workflow to the particular workflow as an input parameter.

For further explanation, FIG. 3 sets forth a block diagram of an example medical image business object (118) according to embodiments of the present invention. The medical image business object (118) of FIG. 3 includes a request ID (302) that includes an identification of the particular request for a medical image processing transaction and a request Type (304) that identifies the kind of image processing transaction being requested. The medical image business object (118) of FIG. 3 also includes an action ID (306) identifying a particular action or workflow to be executed in the image processing transaction. The medical image business object (118) of FIG. 3 provider ID (308) identifying the provider of the medical images to be processed in the image transaction. The medical image business object (118) of FIG. 3 includes image provider protocol (338) that identifies the protocol and standard in which the images and request were created such as DICOM, HL7, and so on as will occur to those of skill in the art.

The medical image business object (118) of FIG. 3 includes a patient ID (310) that identifies the patient. Such an identification may include a name, social security number or other unique identification of the patient. The medical image business object (118) of FIG. 3 includes a physician ID (312) identifying a physician associated with the patient and a technician ID (314) identifying one or more technician that performed the scan to create the medical images associated with the request.

The medical image business object (118) of FIG. 3 include a scanner ID (316) identifying the scanner used to produce the medical images associated with the request. Such an identification may include a manufacturer name, serial number of the scanner or any other identification that will occur to those of skill in the art. The medical image business object (118) of FIG. 3 also includes a scanner type (318) identifying the type of scanner such as magnetic resonance scanners, computer tomography scanners, digital radiography scanners and so forth as will occur to those of skill in the art.

The medical image business object (118) of FIG. 3 includes an image ID (320) identifying the medical image. Such an image ID may also identify the image and the series of images of which the image is a part. The medical image business object (118) of FIG. 3 includes an image type (322) that identifies the type of image. The type of image may also identify the type of images in a series of images.

The medical image business object (118) of FIG. 3 includes a patient location (324) identifying the location of the patient and a destination location (326) identifying the location to which the processed resultant medical images and associated notifications are to be sent.

The medical image business object (118) of FIG. 3 includes a receiving gateway ID (328) identifying the medical imaging gateway in the medical imaging cloud computing environment in which the request for the imaging transaction was received and the destination gateway ID (330) identifying the medical imaging gateway in the medical imaging cloud computing environment to which there response and resultant processed images and notifications are to be sent.

The medical image business object (118) of FIG. 3 includes an original image pointer (332) that points to the original images or series of images in data storage in the medical imaging cloud computing environment. In some embodiments, the original images may be stored on the medical imaging gateway that received the request for the transaction. The medical image business object (118) of FIG. 3 includes an interim image pointer (334) that points to the current state of an image or series of images during the execution of the imaging transaction. Such images may be interim in the sense that some of the workflows for the images have been executed but the image transaction is not complete. The medical image business object (118) of FIG. 3 includes a resultant image pointer (336) that points to the resultant image after completion of the image transaction.

The fields and structure of the medical image business object (118) of FIG. 3 are for explanation and not for limitation. Business objects, interim business objects, and the like useful in embodiments of the present invention may include many different fields and different structure as will occur to those of skill in the art.

Figure 4:
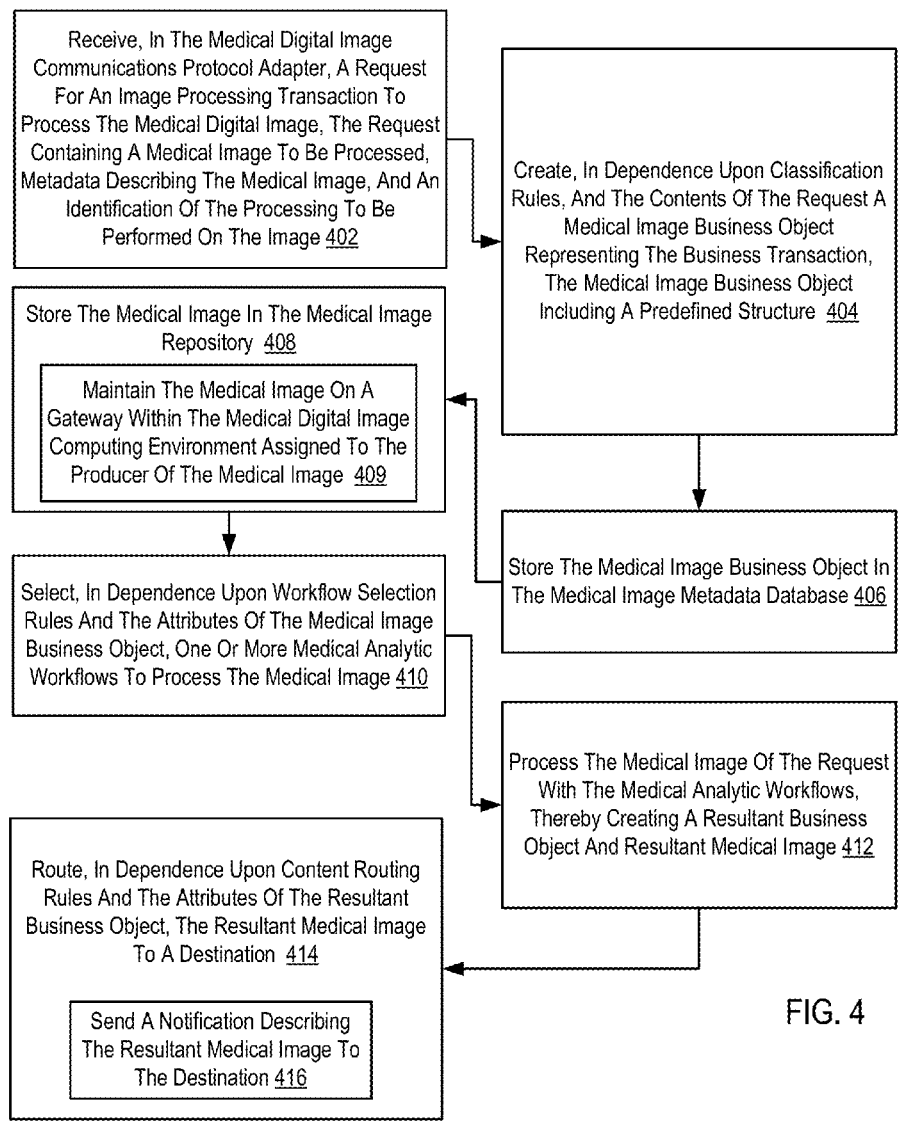
FIG. 4 sets forth a flow chart illustrating an example method of administering medical digital images in a distributed medical digital image computing environment according to embodiments of the present invention.

For further explanation, FIG. 4 sets forth a flow chart illustrating an example method of administering medical digital images in a distributed medical digital image computing environment according to embodiments of the present invention. In some embodiments, the distributed medical digital image computing environment is implemented as a cloud computing environment. The medical digital image computing environment includes a medical digital image communications protocol adapter, a medical image metadata database, a medical image repository, and a medical image transaction workflow dispatcher.

The method of FIG. 4 includes receiving (402), in the medical digital image communications protocol adapter, a request for an image processing transaction to process one or more of the medical digital images. The request contains a medical image to be processed, metadata describing the medical image, and an identification of the processing to be performed on the image. The request is also transmitted according to one of a plurality of a medical image communications protocol supported by medical digital image communications protocol adapter and used by a producer of the medical images.

The method of FIG. 4 includes creating (404), in dependence upon classification rules and the contents of the request, a medical image business object representing the business transaction, the medical image business object including a predefined structure. Classification rules are rules that are tailored to parsing and identifying the type of request according to the protocol and standard in which in which the request was created to extract medical images and metadata. The classification rules are also tailored to develop the medical image business object by including the extracted images and metadata in a predefined structure in the medical image business object. Classification rules allow for disparate metadata, arriving in disparate protocols and standards to be read, understood classified and organized according to a defined structure for the medical image business object.

Creating (404), in dependence upon classification rules and the contents of the request, a medical image business object representing the business transaction according to the method of FIG. 4 may be carried out by extracting from the request metadata describing the image according to the medical image communications protocol of the request and conforming the metadata to the predefined structure of the medical image business object.

The method of FIG. 4 also includes storing (406) the medical image business object in the medical image metadata database. Storing (406) the medical image business object in the medical image metadata database may include storing the medical image business object locally on a medical imaging gateway or providing the business object for storage elsewhere in the distributed processing system.

The method of FIG. 4 also includes storing (408) the medical image in the medical image repository. Storing (408) the medical image in the medical image repository according to the method of FIG. 4 may include maintaining (409) the medical image on a gateway within the medical digital image computing environment assigned to the producer of the medical image.

The method of FIG. 4 also includes selecting (410), in dependence upon workflow selection rules and the attributes of the medical image business object, one or more medical analytic workflows to process the medical image. Workflow selection rules are rules that are tailored to carrying out the image processing transaction on the medical images and the medical image business object according to the request received by the health care provider. Such workflow selection rules identify the necessary requirements of the transaction and select workflows having services that carry out those requirements as well as select workflows that are tailored for the attributes of those images such as the slice size, number of slices, type of scanner used to create the images, standards used for the images and many others as will occur to those of skill in the art. Workflows may include analytics for tumor detection, tumor growth, aneurysm detection, vessel separation in a patients head, and many other medical conditions, workflows for image compression, image resolution, distribution of images, and many other workflows for medical image processing that will occur to those of skill in the art.

The method of FIG. 4 also includes processing (412) the medical image of the request with the medical analytic workflows, thereby creating a resultant business object and resultant medical image. Processing (412) the medical image of the request with the medical analytic workflows may be carried out by executing the selected workflows on the medical images and the medical image business model associated with the requested image processing transaction.

The method of FIG. 4 also includes routing (414), in dependence upon content routing rules and the attributes of the resultant business object, the resultant medical image to a destination. Content routing rules are rules dictating the manner in which resultant medical images are routed to the destination. Such rules are often based on the content of the resultant medical image such that the image is routed to an appropriate health care provider in a manner that conforms to both security and privacy. Often the destination of the image is a different location, logical or physical, from the provider of the original medical image prior to its being processed by the medical digital image transaction cluster. Content routing rules may also dictate the manner in which the health care provider may access the resultant medical images and who may access such images.

Routing (414) the resultant medical image according to the method of FIG. 4 may include extracting metadata from the resultant business object, creating a response to the request the response conforming to a particular digital image communications protocol used for the destination, and transmitting the response according to the particular digital image communications protocol. Routing (414) the resultant medical image to a destination may also include storing the resultant medical image on a gateway within the medical digital image computing environment assigned to the producer of the medical image and transmitting the response according to the particular digital image communications protocol further comprises transmitting in the response data access information to access the resultant medical image on the gateway.

Routing (414), in dependence upon content routing rules and the attributes of the resultant business object, the resultant medical image to a destination according to the method of FIG. 4 also includes sending (416) a notification describing the resultant medical image to the destination. Examples of a such a notification may be an email message or a text message to a health care provider notifying the health care provider that the response to the request is ready for viewing or that the workflows processing the medical images identified aspects of the images that are consistent with a medical condition such as tumor, aneurism, vessel separation, and so on as will occur to those of skill in the art.

Figure 5:
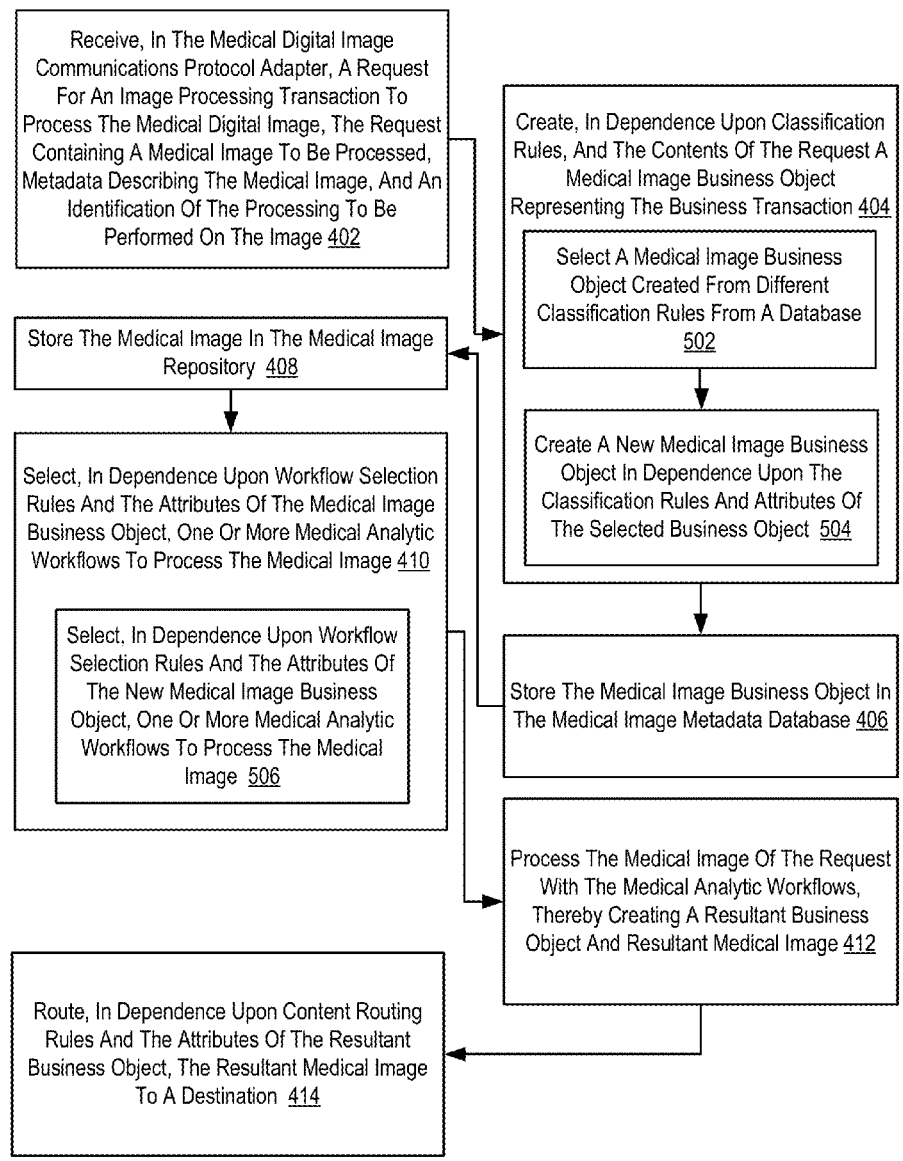
FIG. 5 sets forth a flow chart illustrating and example method of administering medical digital images in a distributed medical digital image computing environment according to embodiments of the present invention.

For further explanation, FIG. 5 sets forth a flow chart illustrating and example method of administering medical digital images in a distributed medical digital image computing environment according to embodiments of the present invention. The method of FIG. 5 is similar to the method of FIG. 4 in that the method of FIG. 5 includes receiving (402), in the medical digital image communications protocol adapter, a request for an image processing transaction to process the medical digital image, creating (404), in dependence upon classification rules and the contents of the request, a medical image business object representing the business transaction, the medical image could business object including a predefined structure; storing (406) the medical image business object in the medical image metadata database; storing (408) the medical image in the medical image repository; selecting (410), in dependence upon workflow selection rules and the attributes of the medical image business object, one or more medical analytic workflows to process the medical image; processing (412) the medical image of the request with the medical analytic workflows, thereby creating a resultant business object and resultant medical image; and routing (414), in dependence upon content routing rules and the attributes of the resultant business object, the resultant medical image to a destination.

The method of FIG. 5 differs from the method of FIG. 4 in that in the method of FIG. 5 creating (404), in dependence upon classification rules, and the contents of the request a medical image business object representing the business transaction further comprises selecting (502) a medical image business object created from different classification rules from a database and creating (504) a new medical image business object in dependence upon the classification rules and attributes of the selected business object.

In the method of FIG. 5 selecting (410), in dependence upon workflow selection rules and the attributes of the medical image business object, one or more medical analytic workflows to process the medical image includes selecting (506), in dependence upon workflow selection rules and the attributes of the new medical image business object, one or more medical analytic workflows to process the medical image.

Figure 6:
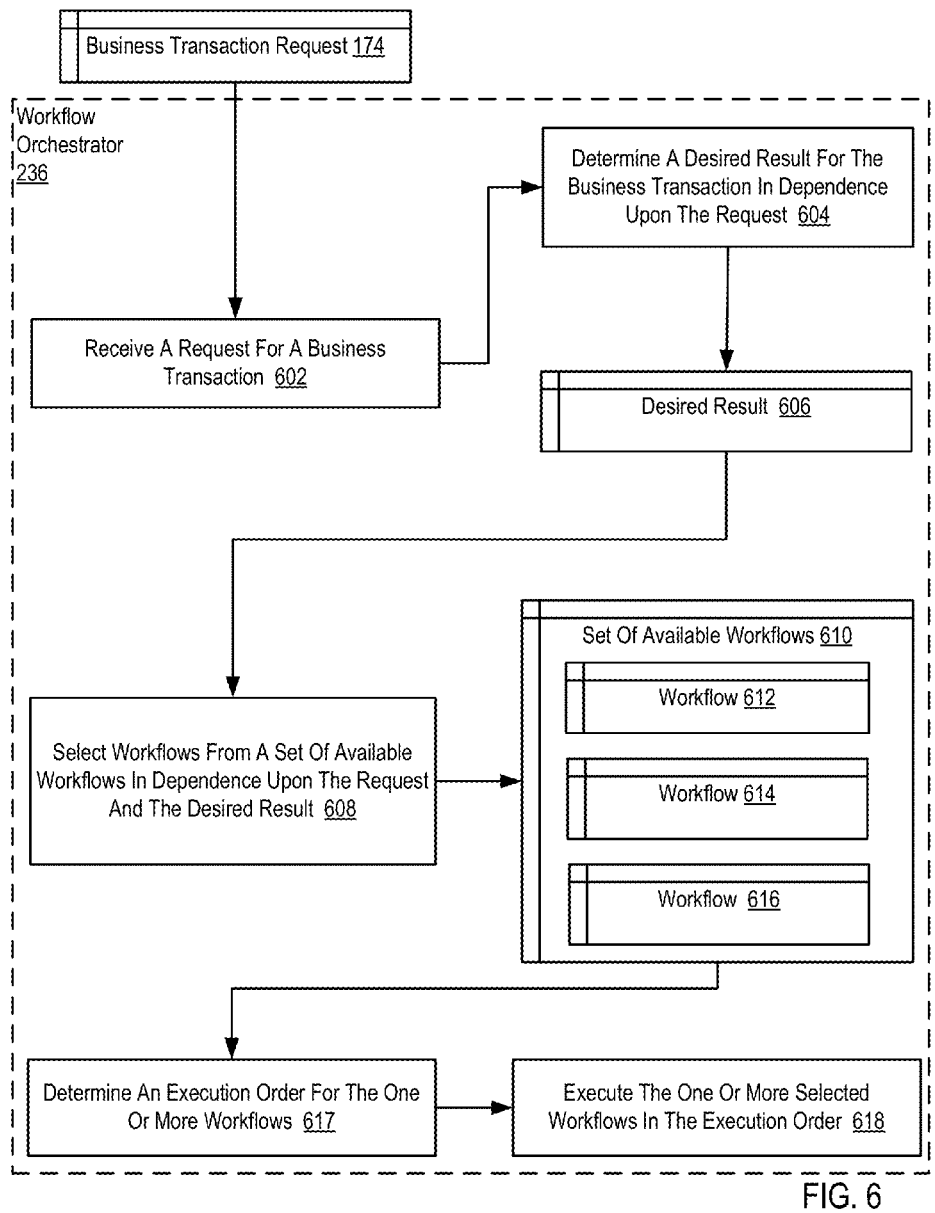
FIG. 6 sets forth a flow chart illustrating an example method of dynamically allocating business workflows according to embodiments of the present invention.

For further explanation, FIG. 6 sets forth a flow chart illustrating an example method of dynamically allocating business workflows according to embodiments of the present invention. The example method of FIG. 6 includes receiving (602) a request (174) for a business transaction. In the example of FIG. 6, the workflow orchestrator (236) receives (602) the request (174) for a business transaction. For example, the workflow orchestrator (236) may receive from a user a request (174) to transmit medical imaging data over a medical cloud computing environment. The workflow orchestrator (236) is capable of receiving the request (174) for execution of a business transaction according to a number of protocols.

The example method of FIG. 6 also includes determining (604) a desired result (606) for the business transaction in dependence upon the request (174). In the example of FIG. 6, each type of request (174) for execution of a business transaction may be associated with a particular output type such that the desired result for the business transaction may correlate to the output type of the request (174) for execution of a business transaction. For example, if the request (174) for execution of a business transaction is a request to transfer a medical image, the desired result for the business transaction may include transferring a medical image.

The example method of FIG. 6 also includes selecting (608) workflows (612, 614, 616) from a set (610) of available workflows in dependence upon the request (174) and the desired result (606). In the example of FIG. 6, the request (174) for execution of a business transaction may include input parameters of a particular type. Furthermore, the request (174) may include metadata describing the request, parameters associated with the request, and so on such that selecting (608) workflows (612, 614, 616) from a set (610) of available workflows in dependence upon the request (174) includes selecting workflows in dependence upon metadata associated with the request (174). Because the desired result has been determined, the workflow orchestrator (236) must therefore select an available workflow (612, 614, 616) that not only takes input parameters of the particular type that are included in the request (174) for execution of a business transaction, but also is capable of generating the desired result alone or in combination with other workflows.

The example method of FIG. 6 also includes determining (617) an execution order for the one or more workflows. In the example of FIG. 6, the execution order of the one or more workflows may be determined (617) such that the output of one workflow is sufficient as input to another workflow, and such that the combination of workflows can turn input received in the request (174) for a business transaction into output of a format that conforms to the desired result (606).

The example method of FIG. 6 also includes executing (618) the selected workflows in the execution order. In the example of FIG. 6, executing the selected workflows may be carried out, for example, by the workflow orchestrator (236) calling a particular workflow and passing information included in the request (174) for execution of a business transaction to the workflow as an input parameter. Alternatively, executing the selected workflows may be carried out by the workflow orchestrator (236) calling a particular workflow and passing information that was returned as output from another workflow to the particular workflow as an input parameter.

Figure 7:
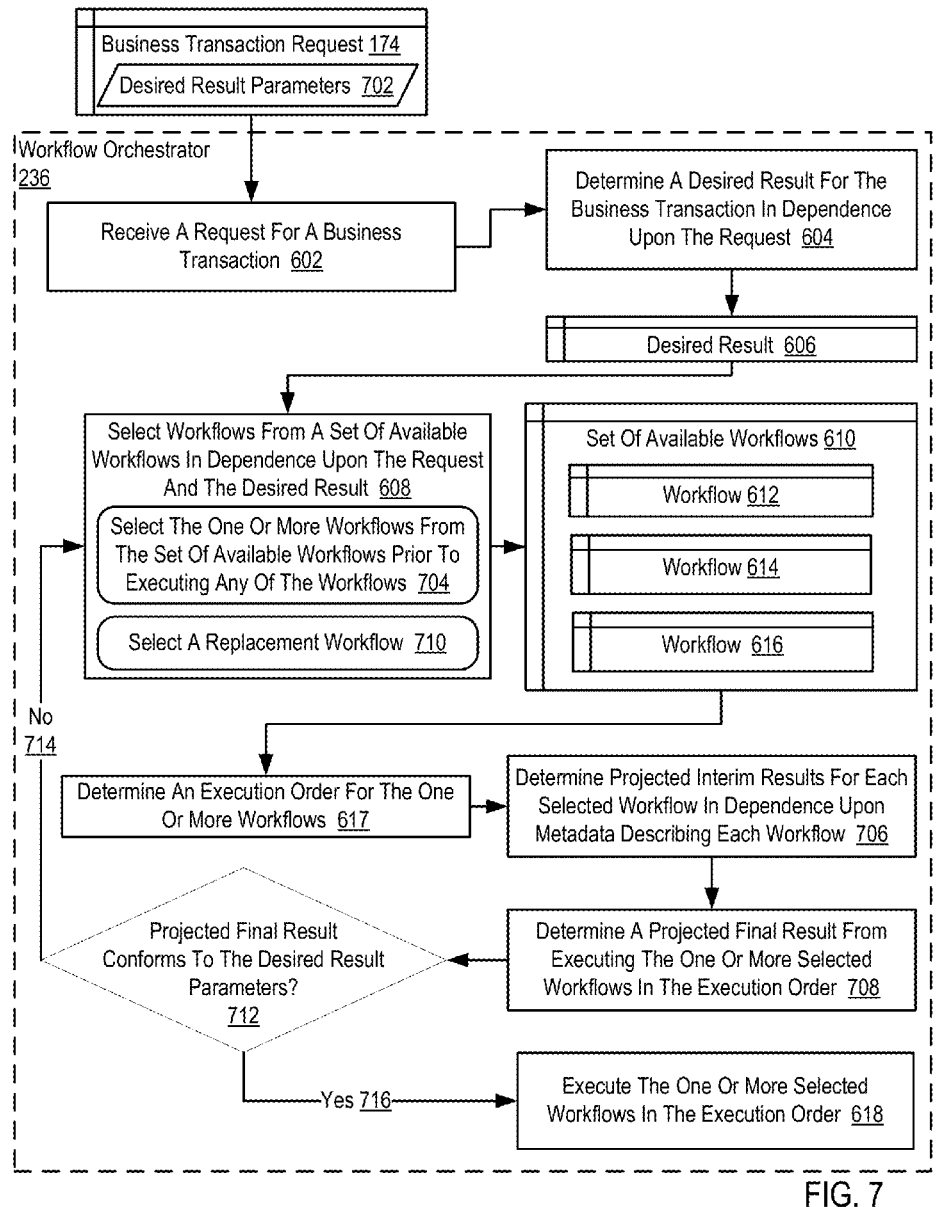
FIG. 7 sets forth a flow chart illustrating a further example method of dynamically allocating business workflows according to embodiments of the present invention.

For further explanation, FIG. 7 sets forth a flow chart illustrating a further example method of dynamically allocating business workflows according to embodiments of the present invention. The example method of FIG. 7 is similar to the example method of FIG. 6 as it also includes:
  receiving (602) a request (174) for a business transaction;
  determining (604) a desired result (606) for the business transaction in dependence upon the request (174);
  selecting (608) workflows from a set (610) of available workflows in dependence upon the request (174) and the desired result (606);
  determining (617) an execution order for the one or more workflows; and
  executing (618) the selected workflows in the execution order.

In the example method of FIG. 7 the request (174) for a business transaction includes desired result parameters (702). In the example of FIG. 7, the desired result parameters (702) may be embodied as data that describes the desired result (606) of executing one or more workflows (612, 614, 616). Consider an example in which the request (174) for a business transaction is a request to transfer medical imaging data. In such an example, the desired result parameters (702) may include a desired image resolution for the medical imaging data, a desired transfer rate for the transfer of medical imaging data, a desired transmission time for the transfer of medical imaging data, and so on.

In the example method of FIG. 7, selecting (608) workflows (612, 614, 616) from a set (610) of available workflows in dependence upon the request (174) and the desired result (606) can includes selecting (704) the one or more workflows (612, 614, 616) from the set (610) of available workflows prior to executing any of the workflows. Metadata describing each workflow may be available such that the inputs and outputs of the available workflows are known. As such, so long as the available inputs to the business transaction are known and the desired outputs of the business transaction are known, one or more workflows may be selected that alone, or in combination, accept input of the type that is available and produce output of the type that is desired. In the example of FIG. 7, the available inputs to the business transaction may be included in the request (174) itself, while the desired outputs of the business transaction may be included in the request (174) in the form of desired result parameters (702) or otherwise determined (604) in the form of the desired result (606).

The example method of FIG. 7 also includes determining (706) projected interim results for each selected workflow in dependence upon metadata describing each workflow. In the example of FIG. 7, the projected interim results for each selected workflow may be embodied as a data type rather than an actual value. That is, metadata describing each workflow may include information identifying the data type of output generated by a particular workflow, such that the interim result for a particular workflow may simply correspond to the data type of output generated by the particular workflow. Because metadata describing each workflow may include information identifying the data type of input expected by a particular workflow, the interim results may be utilized to verify that, for an entire sequence of workflows, each workflow will output data of a particular data type that is acceptable as input data for a subsequently executed workflow. Consider, for example, the following table identifying the set of all available workflows:

TABLE 2

Set of Available Workflows

| Workflow ID | Input Parameter Type | Output Parameter Type |
|---|---|---|
| 1 | A | B |
| 2 | B | A |
| 3 | C | D |
| 4 | D | A |
| 5 | B | D |
| 6 | C | B |

In the example of Table 2, six workflows are identified with workflow IDs of 1, 2, 3, 4, 5, and 6. Consider an example in which a series of workflows is constructed to carry out a business transaction that includes workflow 1, followed by workflow 5, followed by workflow 3. In such an example, the interim result of executing workflow 1 would be data of type 'B.' Because the next workflow to execute (workflow 5) accepts an input parameter of type 'B,' executing workflow 1 and subsequently executing by workflow 5 does not create any obvious problems. The interim result of executing workflow 5 would be data of type 'D.' Because the next workflow to execute (workflow 3) accepts an input parameter of type 'C,' however, this sequence of workflows is not valid. As such, an invalid sequence of workflows has been identified by inspecting the projected interim results that occur during the execution of the sequence of workflows.

The example method of FIG. 7 also includes determining (708) a projected final result from executing the one or more selected workflows in the execution order. In the example of FIG. 7, the projected final result from executing the one or more selected workflows in the execution order may simply correspond to the data type of output generated by the final workflow to be executed in order to carry out a business transaction. In the example of FIG. 7, determining (708) a projected final result from executing the one or more selected workflows in the execution order may therefore be carried out by examining a table identifying the set of all available workflows, such as table 2, and determining the output parameter type of the last workflow of the one or more selected workflows that is to be executed to carry out a particular business transaction.

The example method of FIG. 7 also includes determining (712) whether the projected final result from executing the one or more selected workflows in the execution order conforms to the desired result parameters (702). If the projected final result from executing the one or more selected workflows does (716) conform to the desired result parameters (702), the workflow manager (236) can execute (618) the selected workflows in the execution order. If the projected final result from executing the one or more selected workflows does not (714) conform to the desired result parameters (702), the workflow manager (236) can select (710) a replacement workflow and re-order the new group of selected workflows.

As mentioned above, a cloud computing environment useful in embodiments of the present invention is generally considered service oriented with a focus on statelessness, low coupling, modularity, and semantic interoperability. At the heart of cloud computing is an infrastructure comprising a network of interconnected nodes. For further explanation, FIG. 8 sets forth a block diagram of an example of a cloud computing node useful according to embodiments of the present invention. Cloud computing node (10) is only one example of a suitable cloud computing node and is not intended to suggest any limitation as to the scope of use or functionality of embodiments of the invention described herein. Regardless, cloud computing node (10) is capable of being implemented and/or performing any of the functionality set forth hereinabove.

The cloud computing node (10) is operational with numerous other general purpose or special purpose computing system environments or configurations. Examples of well-known computing systems, environments, and/or configurations that may be suitable for use with the cloud computing node (10) include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

The cloud computing node (10) may be described in the general context of computer system-executable instructions, such as program modules, being executed by a computer system. Generally, program modules may include routines, programs, objects, components, logic, data structures, and so on that perform particular tasks or implement particular abstract data types. The cloud computing node (10) may be practiced in distributed cloud computing environments where tasks are performed by remote processing devices that are linked through a communications network. In a distributed cloud computing environment, program modules may be located in both local and remote computer system storage media including memory storage devices.

Figure 8:
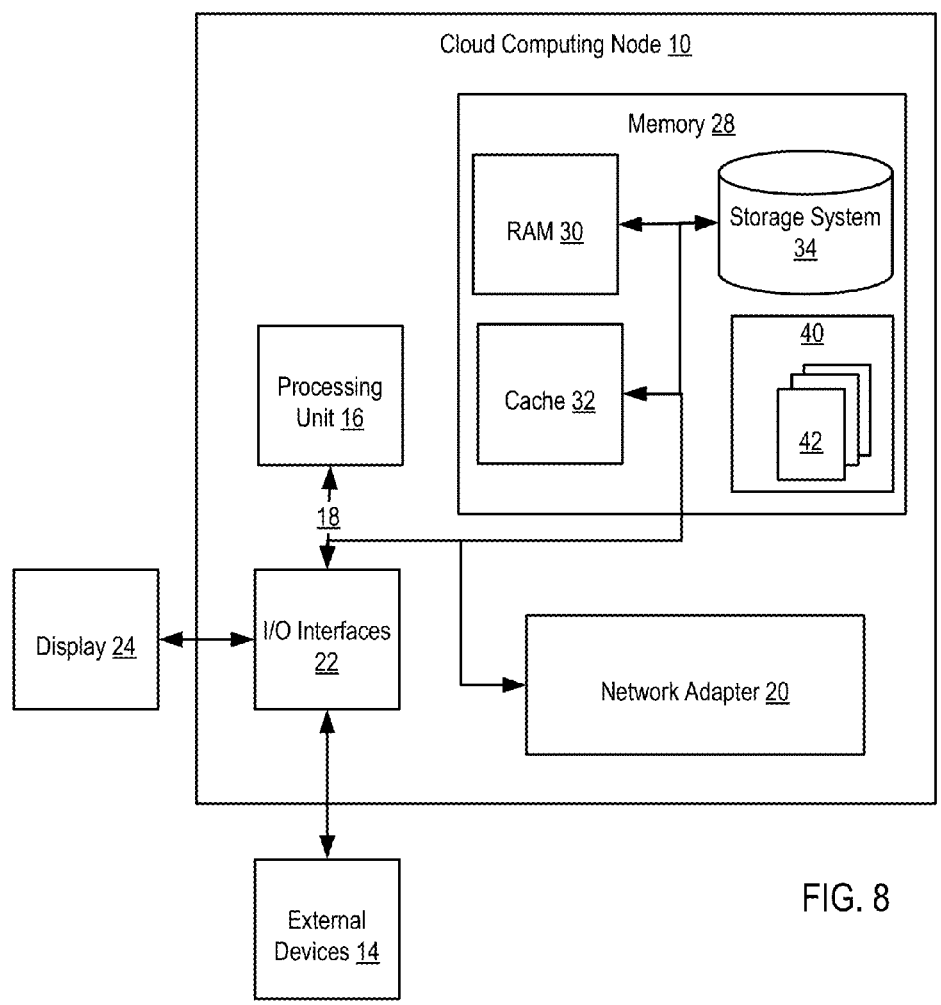
FIG. 8 sets forth a block diagram of an example of a cloud computing node useful according to embodiments of the present invention.

As shown in FIG. 8, the cloud computing node (10) is shown in the form of a general-purpose computing device. The components of the cloud computing node (10) may include, but are not limited to, one or more processors or processing units (16), a system memory (28), and a bus (18) that couples various system components including the system memory (28) to the processor (16).

The bus (18) in the example of FIG. 8 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture ('ISA') bus, Micro Channel Architecture ('MCA') bus, Enhanced ISA ('EISA') bus, Video Electronics Standards Association ('VESA') local bus, and Peripheral Component Interconnects ('PCI') bus.

The cloud computing node (10) of FIG. 8 often includes a variety of computer system readable media. Such media may be any available media that is accessible by the cloud computing node (10), and it includes both volatile and non-volatile media, removable and non-removable media.

The system memory (28) in the example of FIG. 8 can include computer system readable media in the form of volatile memory, such as random access memory ('RAM') (30) and/or cache memory (32). The cloud computing node (10) may further include other removable/non-removable, volatile/non-volatile computer system storage media. By way of example only, a storage system (34) can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, the memory (28) may include at least one program product having a set (e.g., at least one) of program modules that are configured to carry out the functions of embodiments of the invention.

The example of FIG. 8 includes a program/utility (40) having a set (at least one) of program modules (42) that may be stored in the memory (28). The cloud computing node (10) of FIG. 8 may also include an operating system, one or more application programs, other program modules, and program data. Each of the operating system, one or more application programs, other program modules, and program data or some combination thereof, may include an implementation of a networking environment. Program modules (42) generally carry out the functions and/or methodologies of embodiments of the invention as described herein.

The cloud computing node (10) of FIG. 8 may also communicate with one or more external devices (14) such as a keyboard, a pointing device, a display (24), and so on that enable a user to interact with the cloud computing node (10). The cloud computing node (10) may also include any devices (e.g., network card, modem, etc.) that enable the cloud computing node (10) to communicate with one or more other computing devices. Such communication can occur, for example, via I/O interfaces (22). Still yet, the cloud computing node (10) can communicate with one or more networks such as a local area network (IAN), a general wide area network ('WAN'), and/or a public network (e.g., the Internet) via network adapter (20). As depicted, network adapter (20) communicates with the other components of the cloud computing node (10) via the bus (18). It should be understood that although not shown, other hardware and/or software components could be used in conjunction with the cloud computing node (10). Examples include, but are not limited to, microcode, device drivers, redundant processing units, external disk drive arrays, RAID systems, tape drives, and data archival storage systems, and so on.

Figure 9:
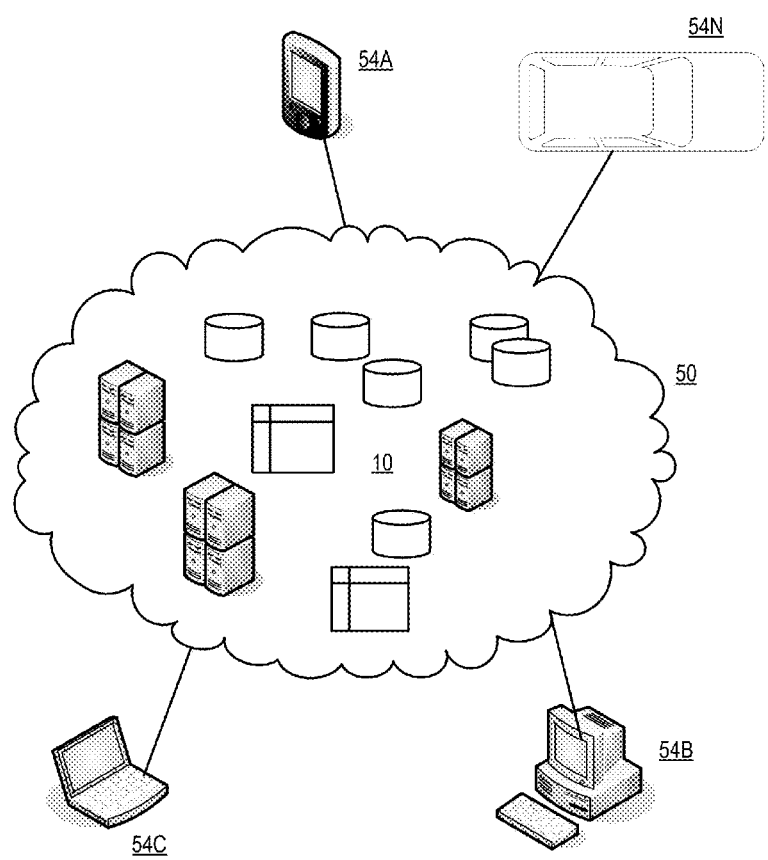
FIG. 9 sets forth a line drawing of an example cloud computing environment.

For further explanation, FIG. 9 sets forth a line drawing of an example cloud computing environment (50). The cloud computing environment (50) of FIG. 9 comprises one or more cloud computing nodes (10) with which local computing devices used by cloud consumers, such as, for example, personal digital assistant (PDA) or cellular telephone (54A), desktop computer (54B), laptop computer (54C), and/or automobile computer system (54N) may communicate. The cloud computing nodes (10) may communicate with one another. They may be grouped (not shown) physically or virtually, in one or more networks, such as private, community, public, or hybrid clouds as described hereinabove, or a combination thereof. This allows cloud computing environment (50) to offer infrastructure, platforms and/or software as services for which a cloud consumer does not need to maintain resources on a local computing device. It is understood that the types of computing devices (54A-N) shown in FIG. 9 are intended to be illustrative only and that computing nodes (10) and cloud computing environment (50) can communicate with any type of computerized device over any type of network and/or network addressable connection (e.g., using a web browser).

Figure 10:
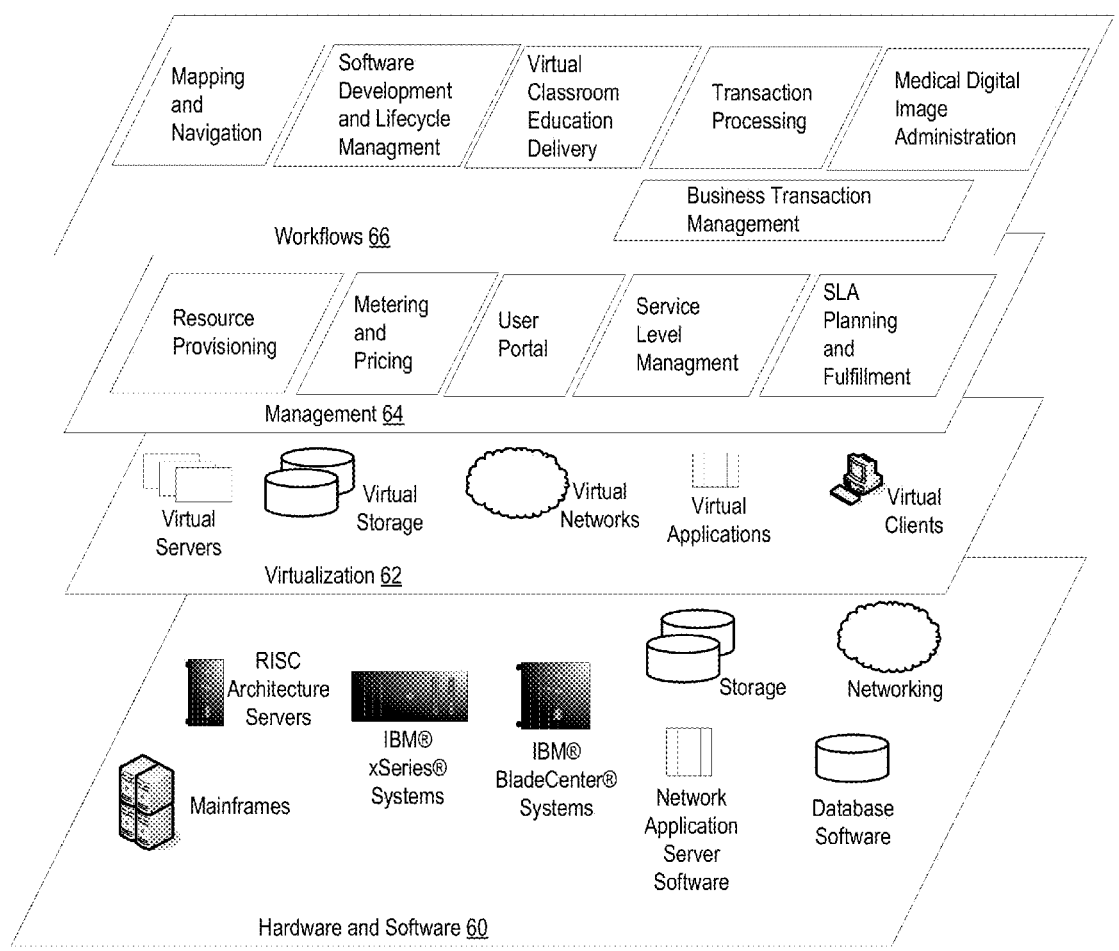
FIG. 10 sets forth a line drawing showing an example set of functional abstraction layers provided by cloud computing environment.

For further explanation, FIG. 10 sets forth a line drawing showing an example set of functional abstraction layers provided by cloud computing environment (50 in FIG. 9). It should be understood in advance that the components, layers, and functions shown in FIG. 10 are intended to be illustrative only and embodiments of the invention are not limited thereto. As depicted, the following layers and corresponding functions are provided:

The example of FIG. 10 includes a hardware and software layer (60). Hardware and software layer (60) in the example of FIG. 10 includes hardware and software components. Examples of hardware components include mainframes, in one example IBM® zSeries® systems; RISC (Reduced Instruction Set Computer) architecture based servers, in one example IBM pSeries® systems; IBM xSeries® systems; IBM BladeCenter® systems; storage devices; networks and networking components. Examples of software components include network application server software, in one example IBM WebSphere® application server software; and database software, in one example IBM DB2® database software. (IBM, zSeries, pSeries, xSeries, BladeCenter, WebSphere, and DB2 are trademarks of International Business Machines Corporation registered in many jurisdictions worldwide)

The example of FIG. 10 includes a virtualization layer (62). The virtualization layer (62) of FIG. 10 provides an abstraction layer from which the following examples of virtual entities may be provided: virtual servers; virtual storage; virtual networks, including virtual private networks; virtual applications and operating systems; and virtual clients.

The example of FIG. 10 also includes a management layer (64). The management layer (64) may provide the functions described below. Resource provisioning provides dynamic procurement of computing resources and other resources that are utilized to perform tasks within the cloud computing environment. Metering and pricing provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provide pre-arrangement for, and procurement of, cloud computing resources for which a future requirement is anticipated in accordance with an SLA.

The example of FIG. 10 also includes a workflows layer (66). The workflows layer (66) of FIG. 10 provides examples of functionality for which the cloud computing environment may be utilized. Examples of workflows and functions which may be provided from this layer include: mapping and navigation; software development and lifecycle management; virtual classroom education delivery; data analytics processing; and transaction processing.

The workflows layer (66) includes administering medical digital images according to embodiments of the present invention include receiving, in the medical digital image communications protocol adapter, a request for an image processing transaction to process the medical digital image, the request containing a medical image to be processed, metadata describing the medical image, and an identification of the processing to be performed on the image; and wherein the request is transmitted according to one of a plurality of a medical image communications protocol supported by medical digital image communications protocol adapter and used by a producer of the medical images; creating, in dependence upon classification rules and the contents of the request, a medical image business object representing the business transaction, the medical image could business object including a predefined structure; storing the medical image business object in the medical image metadata database; storing the medical image in the medical image repository; selecting, in dependence upon workflow selection rules and the attributes of the medical image business object, one or more medical analytic workflows to process the medical image; processing the medical image of the request with the medical analytic workflows, thereby creating a resultant business object and resultant medical image; routing, in dependence upon content routing rules and the attributes of the resultant business object, the resultant medical image to a destination wherein routing the resultant medical image includes extracting metadata from the resultant business object, creating a response to the request the response conforming to a particular digital image communications protocol used for the destination, and transmitting the response according to the particular digital image communications protocol.

The workflows layer (66) includes business transaction management including business transaction capture and replay with long term request persistence according to embodiments of the present invention including creating, in response to a request for execution of a business transaction, an original business object representing the request for execution of a business transaction, the business object having a data structure supported by the business transaction; executing one or more business processes of the business transaction on the original business object including storing the interim results of each business process as an interim business object; maintaining, in a failed request business object, the original business object and the interim business object; identifying a failure of a business process; including, in the failed request business object, error information about the failed business process; and re-executing the business transaction using the failed request business object.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowcharts and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

It will be understood from the foregoing description that modifications and changes may be made in various embodiments of the present invention without departing from its true spirit. The descriptions in this specification are for purposes of illustration only and are not to be construed in a limiting sense. The scope of the present invention is limited only by the language of the following claims.

What is claimed is:

1. A system comprising one or more computer processors and computer memory operatively coupled to the computer processors, the computer memory having disposed within it computer program instructions that, when executed by the one or more computer processors, cause the one or more computer processors to carry out the steps of:
    receiving, by a workflow orchestrator that includes automated computing machinery, a request for a transmission of a medical image formatted according a medical image protocol, including receiving one or more desired result parameters in the request, wherein the desired result parameters comprise a desired image resolution for the medical image;
    determining, by the workflow orchestrator, a desired result for the transmission in dependence upon the request and the one or more desired result parameters, including identifying a desired output type;
    configuring, based on initial input parameters and the determined desired result, a hardware processing component cluster to process the medical image with particular hardware data processing components within the cluster, in a particular execution order including dynamically allocating hardware data processing components, using the medical image as initial input parameters and the determined desired result, including:
        selecting, by the workflow orchestrator, one or more hardware data processing components from a set of available hardware data processing components in dependence upon the request and the desired result;
        determining an execution order for the one or more hardware data processing components, wherein determining the execution order comprises determining that an output of a first hardware data processing component is sufficient as input for a second hardware data processing component;
        determining a projected final result from executing the one or more selected hardware data processing components in the particular execution order, wherein determining the projected final result comprises examining a table identifying the set of available hardware data processing components and determining an output parameter type of a last hardware data processing component in the execution order;
        selecting a different hardware data processing component in response to determining that the projected final result from executing the one or more selected hardware data processing components in the execution order does not conform to the desired result parameters;
        reordering, by the workflow orchestrator, the one or more selected hardware data processing components and the different hardware data processing component in the execution order; and
    executing, by the workflow orchestrator, the one or more selected hardware data processing components in the execution order including calling a particular hardware data processing component and passing data that was returned as output from another hardware data processing component to the particular hardware data processing component as an input parameter.

2. The system of claim 1 wherein selecting, by the workflow orchestrator, one or more hardware data processing components from a set of available data processing components in dependence upon the request and the desired result includes selecting the one or more data processing components from the set of available data processing components prior to executing any of the data processing components.

3. The system of claim 1 further comprising computer program instructions that, when executed by the one or more computer processors, cause the one or more computer processors to carry out the step of determining projected interim results for each selected data processing component in dependence upon metadata describing each data processing component.

4. A computer program product including a computer readable medium, wherein the computer readable medium is not a signal, the computer program product comprising computer program instructions that, when executed, of cause a computer to carry out the steps of:
    receiving, by a workflow orchestrator that includes automated computing machinery, a request for a transmission of a medical image formatted according a medical image protocol, including receiving one or more desired result parameters in the request, wherein the desired result parameters comprise a desired image resolution for the medical image;
    determining, by the workflow orchestrator, a desired result for the transmission in dependence upon the request and the one or more desired result parameters, including identifying a desired output type;
    configuring, based on initial input parameters and the determined desired result, a hardware processing component cluster to process the medical image with particular hardware data processing components within the cluster, in a particular execution order including dynamically allocating hardware data processing components, using the medical image as initial input parameters and the determined desired result, including:
        selecting, by the workflow orchestrator, one or more hardware data processing components from a set of available hardware data processing components in dependence upon the request and the desired result;

determining an execution order for the one or more hardware data processing components, wherein determining the execution order comprises determining that an output of a first hardware data processing component is sufficient as input for a second hardware data processing component;

determining a projected final result from executing the one or more selected hardware data processing components in the particular execution order, wherein determining the projected final result comprises examining a table identifying the set of available hardware data processing components and determining an output parameter type of a last hardware data processing component in the execution order;

selecting a different hardware data processing component in response to determining that the projected final result from executing the one or more selected hardware data processing components in the execution order does not conform to the desired result parameters;

reordering, by the workflow orchestrator, the one or more selected hardware data processing components and the different hardware data processing component in the execution order; and executing, by the workflow orchestrator, the one or more selected hardware data processing components in the execution order including calling a particular hardware data processing component and passing data that was returned as output from another hardware data processing component to the particular hardware data processing component as an input parameter.

5. The computer program product of claim 4 wherein selecting, by the workflow orchestrator, one or more hardware data processing components from a set of available data processing components in dependence upon the request and the desired result includes selecting the one or more data processing components from the set of available data processing components prior to executing any of the data processing components.

6. The computer program product of claim 4 further comprising computer program instructions that, when executed, cause a computer to carry out the step of determining projected interim results for each selected data processing component in dependence upon metadata describing each data processing component.

* * * * *